(12) United States Patent
Lastarria

(10) Patent No.: US 9,956,040 B1
(45) Date of Patent: May 1, 2018

(54) LASER SURGERY SYSTEM WITH SAFETY CONTROL OF NON-TARGET TISSUE TEMPERATURE AND METHOD OF USE

(71) Applicant: Emilio F. Lastarria, Miami, FL (US)

(72) Inventor: Emilio F. Lastarria, Miami, FL (US)

( * ) Notice: Subject to any disclaimer, the term of this patent is extended or adjusted under 35 U.S.C. 154(b) by 197 days.

(21) Appl. No.: 14/866,996

(22) Filed: Sep. 27, 2015

Related U.S. Application Data

(60) Provisional application No. 62/057,521, filed on Sep. 30, 2014.

(51) Int. Cl.
*A61B 18/22* (2006.01)
*A61B 18/00* (2006.01)

(52) U.S. Cl.
CPC .... *A61B 18/22* (2013.01); *A61B 2018/00029* (2013.01); *A61B 2018/00517* (2013.01); *A61B 2018/00547* (2013.01); *A61B 2018/00577* (2013.01); *A61B 2018/00642* (2013.01); *A61B 2018/00678* (2013.01); *A61B 2018/00708* (2013.01); *A61B 2018/00791* (2013.01); *A61B 2018/00898* (2013.01)

(58) Field of Classification Search
CPC .......... A61B 18/22; A61B 2018/00029; A61B 2018/00517; A61B 2018/00547; A61B 2018/00577; A61B 2018/00642; A61B 2018/00678; A61B 2018/00708; A61B 2018/00791; A61B 2018/00898
USPC .......................................................... 606/12
See application file for complete search history.

(56) References Cited

U.S. PATENT DOCUMENTS

| 5,437,673 | A | * | 8/1995 | Baust | A61F 7/12 604/30 |
|---|---|---|---|---|---|
| 5,496,271 | A | * | 3/1996 | Burton | A61B 18/18 604/101.05 |
| 6,986,764 | B2 | * | 1/2006 | Davenport | A61B 18/22 600/2 |
| 2002/0022829 | A1 | * | 2/2002 | Nagase | A61B 18/20 606/12 |
| 2002/0077680 | A1 | * | 6/2002 | Noda | A61B 17/00 607/105 |
| 2009/0216300 | A1 | * | 8/2009 | Keltner | A61N 5/0601 607/89 |

(Continued)

*Primary Examiner* — Gary Jackson
*Assistant Examiner* — Zahed Kabir
(74) *Attorney, Agent, or Firm* — CUSPA Technology Law Associates; Yi Li

(57) ABSTRACT

A laser ablation surgery system with a safety control of non-target tissue temperature and laser ablation surgery method are provided. The system includes a laser source configured to produce a laser beam at a wavelength absorbable by a target issue through an optical fiber connected thereto, a temperature sensor disposed at an irrigation fluid outlet of a flow sheath of a continuous flow endoscope, and a system control operably connected to the laser source and the temperature sensor. The temperature sensor is configured to monitor the temperature of an effluent exiting a body cavity adjacent to the target issue during a laser ablation surgery. The system control includes at least one predetermined effluent temperature threshold and a laser control mechanism. The system control is configured to activate the laser control mechanism when the temperature sensor senses the temperature of the effluent exceeding the predetermined effluent temperature threshold.

17 Claims, 2 Drawing Sheets

(56) References Cited

U.S. PATENT DOCUMENTS

| | | | | |
|---|---|---|---|---|
| 2010/0262137 A1* | 10/2010 | Nye | ............... | A61B 18/18 606/33 |
| 2014/0052224 A1* | 2/2014 | Kassab | ............... | A61F 7/123 607/105 |

* cited by examiner

LASER SURGERY SYSTEM WITH SAFETY CONTROL OF NON-TARGET TISSUE TEMPERATURE AND METHOD OF USE

CROSS REFERENCE TO RELATED APPLICATION

This application claims the benefit under 35 USC 119 (e) of the provisional patent application Ser. No. 62/057,521, filed Sep. 30, 2014, which is hereby incorporated by reference in its entirety.

FIELD OF THE INVENTION

The present invention relates to a laser surgery system, more specifically relates to a laser ablation surgery system with a safety control of non-target tissue temperature and method of use.

BACKGROUND OF THE INVENTION

Laser ablation has been used in surgical procedures for treating various clinical conditions. Photoselective vaporization of the prostate (PVP) is a laser ablation surgery for treating an enlarged prostate (benign prostatic hyperplasia).

During a PVP surgery, a surgeon inserts an optical fiber into the urethra through a continuous flow cystoscope. A high-power green light laser beam is emitted through an optical fiber to vaporize and precisely remove enlarged prostate tissue. During the surgery, an irrigation fluid is provided into the bladder through a flow sheath in the cystoscope to maintain a clear field of vision, and to cool the laser optical fiber and surrounding tissues for preventing overheating of the bladder and prostate during the laser ablation of the prostate due to heat transfer. Because the tissue is vaporized and removed, a wide-open channel is created. The urine flow is improved and bothersome urinary symptoms are decreased.

PVP surgery is an effective and less invasive alternative to older, more traditional methods of removing prostate obstructions. After the surgery, most patients are released in less than 24 hours, in many cases without a catheter, and recovery time is shorter. Because PVP surgery vaporizes tissue rather than cutting or resecting it, there's generally less blood loss, particularly beneficial to men who have blood-clotting conditions or those who take blood thinners. In the past ten years, thousands of PVP procedures have been successfully performed to treat patients who suffer from symptoms of benign prostatic hyperplasia.

However, since PVP surgery is relatively new, side effects and potential complications and risks due to exposure of the surrounding tissue to elevated temperature over extended period time of the ablation procedure have not been fully studied or understood. It is assumed that the bladder cavity serves as a protective heat sink that absorbs and dissipates the excessive thermal energy generated by the laser ablation surgery. It is known that during the PVP procedure, the temperature inside the bladder rises substantially even in the presence of the irrigation fluid. After applying high energy GreenLight laser to the prostate continuously for a period of time, such as 5-20 minutes, effluent exiting the bladder through the fluid outlet of cystoscope becomes hot. Sometimes, the ablation process takes more than 60 minutes, therefore, the temperature inside the bladder rises to such an extent under which the bladder may incur a thermal injury.

It has been observed that heat transfer due to a prolonged PVP procedure can result in immersion scalding injury to adjacent non-target tissue.

Commonly, an irrigation is provided using a sterile saline solution contained in a flexible bag, which is connected to the continuous flow cystoscope through a tubing. The flow rate is manually controlled by the surgeon and surgical staff, and the bag may need to be replaced when the solution runs out. When the flow rate is insufficient for heat dissipation, the temperature inside the bladder could rise to the degree that could cause a thermal injury to the bladder. Burns of the inner lining of the bladder has been observed following PVP surgery when the irrigation fluid is insufficient and/or transiently not provided due to mechanical problem or operation error, which resulted in painful post-surgery complications. Irreversible changes and the severity of epithelial and deep tissue injury can be a function of the temperature to which the tissue is exposed to and duration of the exposure.

Currently, laser ablation equipment used for PVP surgery operates independently from the management of irrigation of the bladder. No device is available for monitoring or controlling the temperature in the bladder for the PVP surgery. Management of the irrigation fluid to compensate for the heating to the bladder during the surgery is provided manually based on surgeon's observation and experiences. This presents a significant risk to patient safety due to a potential human error or mechanical failure in managing the irrigation fluid.

Therefore, there is a strong need for an improved laser ablation surgical system and safety measurement that overcomes the above mentioned deficiencies.

SUMMARY OF THE INVENTION

In one embodiment, the present invention is directed to a laser ablation surgery system with a safety control of non-target tissue temperature. The system comprises a laser source configured to produce a laser beam at a wavelength absorbable by a target issue through an optical fiber connected thereto; a temperature sensor disposed at an irrigation fluid outlet of a flow sheath of a continuous flow endoscope, the temperature sensor being configured to monitor a temperature of an effluent exiting a body cavity adjacent to a target issue during a laser ablation surgery; and a system control operably connected to the laser source and the temperature sensor. The system control comprises at least one predetermined effluent temperature threshold and a laser control mechanism. The system control is configured to activate the laser control mechanism when the temperature sensor senses the temperature of the effluent exceeding the predetermined effluent temperature threshold.

In another embodiment, the present invention is directed to a method of laser ablation surgery using the system of the present invention. The method comprises performing a laser ablation surgery on a target tissue using the laser ablation surgery system described above, and monitoring the temperature of the effluent exiting the body cavity during the laser ablation surgery by the temperature sensor of the system, wherein the system control activates the laser control mechanism when the temperature sensor senses the temperature of the effluent exceeding the predetermined effluent temperature threshold, thereby preventing a thermal injury to the body cavity due to heat transfer.

In a further embodiment, the present invention is directed to a further method of laser ablation surgery. The method comprises performing a laser ablation surgery on a target tissue with a continuous flow endoscope using an optical fiber connected to a laser source configured to produce a laser beam at a wavelength absorbable by the target issue, providing a temperature sensor at an irrigation fluid outlet of the endoscope configured to monitor a temperature of an effluent exiting a body cavity adjacent to the target tissue; and monitoring the temperature of the effluent exiting the body cavity by the temperature sensor during the laser ablation surgery on the target tissue, and adjusting emission of the laser source when the temperature sensor senses the temperature of the effluent exceeding a predetermined effluent temperature threshold, thereby preventing a thermal injury to the body cavity due to heat transfer.

The advantages of the present invention will become apparent from the following description taken in conjunction with the accompanying drawings showing exemplary embodiments of the invention.

DETAILED DESCRIPTION OF THE INVENTION

Figure 1:
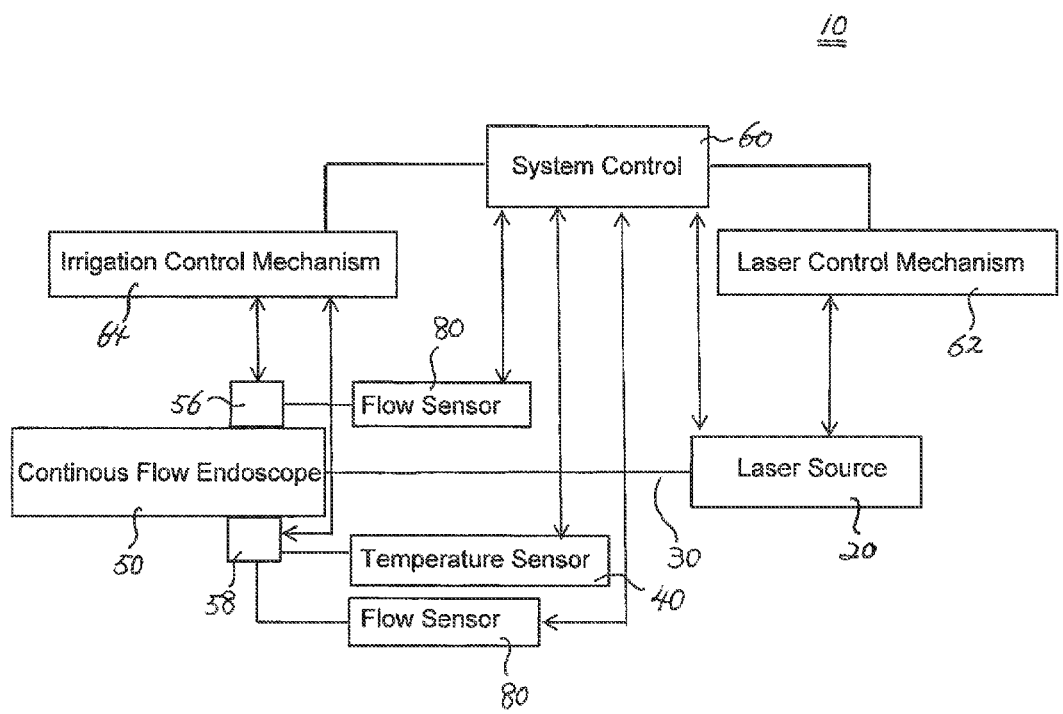
FIG. 1 is a schematic block diagram of the laser ablation surgery system in one embodiment of the present invention.

In one embodiment, the present invention provides a laser ablation surgery system with a safety control of non-target tissue temperature. In one embodiment as shown in FIG. 1, the laser ablation surgery system 10 comprises a laser source 20, at least one temperature sensor 40 and a system control 60.

The laser source 20 is configured to produce a laser beam through an optical fiber 30 connected thereto. The laser source can be solid state or other forms of laser. In one embodiment, a solid state potassium-titanyl-phosphate (KTP) laser with a continuous wave beam is used. The laser beam is at a wavelength absorbable by the target issue that is subjected to the laser ablation surgery. In one embodiment, the wavelength of the laser beam is at about 532 nm, which is highly absorbable by hemoglobin of the red blood cells in the region of the target tissue. Other wavelengths absorbable by specific target tissues can also be used for laser ablation.

The power output of the laser beam is configured for laser ablation of soft tissue, as well as for coagulation. In one embodiment, the power output of the laser beam is between 30 and 180 watts. The laser beam can have different operating modes, for example, ablation or vaporization mode, and coagulation mode. In the vaporization mode, typically a power output about 80-180 W is used to burn and vaporize the target tissue. In the coagulation mode, typically a power output about 5-40 W is used to cauterize or cause coagulation of veins in the region of the target tissue to prevent or stop bleeding.

The optical fiber used for the laser ablation surgery is typically sterilized single use non-contact laser fiber optic. The fiber core diameter, the fiber tip dimension and the firing angle can be configured according to the need to the laser ablation surgery. In one embodiment, the optical fiber has a fiber core diameter about 750 μm, an outer diameter of the fiber tip of about 2.3 mm, a length about 12 feet, a firing angle of about 70-80 degrees, and power range less than 180 W.

The optical fiber is placed into a work port of a continuous flow endoscope 50 and the opposing end is connected to the laser source by a surgeon before the surgery. Various commercially available continuous flow endoscopes, such as GreenLight laser cystoscope manufactured by Richard Wolf, and OES Pro continuous flow laser-cystoscope manufactured by Olympus, are suitable to be used with the optical fiber for the purpose of the present invention.

The continuous flow endoscope has an elongated probe that includes therein a flow sheath, an optical cable with a lens for viewing the surgical site and for imaging, and one or more additional tubes for guiding other instruments for surgical procedures. The latter is commonly referred to as working port. The flow sheath includes an irrigation fluid inlet 56 and irrigation fluid outlet 58 disposed at the proximal end of the elongated probe, which are also referred to as inlet port and outlet port. In one embodiment, the flow sheath includes an inner sheath and an outer sheath, disposed coaxially with each other, and the irrigation fluid inlet 56 and outlet 58 are connected to the proximal end of the outer sheath.

In one embodiment, a temperature sensor 40 is disposed at the irrigation fluid outlet 58 of the flow sheath, and is configured to monitor the temperature of the effluent that exits a body cavity adjacent to the target issue during the laser ablation surgery. Herein, the term of non-target tissue refers to the tissue that is not the subject of the laser ablation surgery, yet located adjacent to the target tissue. The body cavity referred to herein is a cavity adjacent to the target issue of a laser ablation surgery, and is suitable for irrigation by a fluid. Various known temperature sensing mechanisms can be used for the purpose of the present invention, for example, thermocouples, resistance temperature sensors, and infrared sensors. The temperature sensors can also be wireless.

In one embodiment, temperature sensor 40 has a sensing probe which is configured to be in a direct contact with the effluent immediately flowing out from the irrigation fluid outlet. Moreover, the sensing probe can be immersed in or attached to a flow chamber connected to the irrigation fluid outlet Temperature sensor 40 and laser source 20 are operably connected to system control 60. System control 60 comprises a laser control mechanism 62 and one or more predetermined effluent temperature thresholds. System control 60 is configured to activate the laser control mechanism 62 when temperature sensor 40 senses the temperature of the effluent exceeding a predetermined effluent temperature threshold. In one embodiment, system control 60 includes a microprocessor incorporating therein one or more predetermined effluent temperature thresholds. The predetermined effluent temperature thresholds can be preset by the manufacturer of the laser ablation system, or inputted by the operator according to the need of a specific surgery.

In one embodiment, a first predetermined effluent temperature threshold is a warning effluent temperature, and a second predetermined effluent temperature threshold is a critical effluent temperature. When the effluent at the irrigation fluid outlet reaches the critical effluent temperature, it indicates the temperature inside the body cavity has reached a critical thermal injury temperature, at which the body cavity will be subjected to thermal injury. The warning effluent temperature is below the critical effluent temperature, and the difference between the two temperatures can be determined empirically according to the surgical procedure to be performed.

Once temperature sensor 40 senses that the effluent at the irrigation fluid outlet has reached the warning effluent temperature, the laser control mechanism 60 sends a warning signal to the user, or automatically reduces the power output of the laser source. The warning signal can be a light or an audio signal. Once the temperature sensor 40 senses that the effluent at the irrigation fluid outlet has reached the critical effluent temperature, the laser control mechanism 62 stops emission from laser source 20 to prevent further rising of temperature in the body cavity. Moreover, at the critical effluent temperature, the laser control mechanism 62 can further send one or more warning signals to indicate the critical effluent temperature and/or the stop of laser emission because of the critical effluent temperature.

The temperature sensor 40 configured at the irrigation fluid outlet is non-invasive and the temperature of the body cavity can be monitored in real time conveniently using the effluent as a medium. Moreover, the temperature sensor at the irrigation fluid outlet is not exposed to laser beam emitted during the laser ablation procedure, therefore, no interference from heat generated by the laser.

It should be understood that the critical effluent temperature of the effluent at the irrigation fluid outlet is close to, but may not be identical to the critical thermal injury temperature inside the body cavity. The irrigation fluid travels from the inside of the body cavity through the flow sheath to the irrigation fluid outlet. Due to the temperature difference between the temperature inside the body cavity and the ambient temperature and travel distance, the effluent temperature at the irrigation fluid outlet may be lower than that inside the body cavity. The extent of the temperature difference depends on the ambient temperature, travel distance, and the flow rate. The temperature inside the body cavity can be measured by introducing a separate temperature sensor through the working port into the body cavity. Once the temperature difference is determined, the critical effluent temperature can be established, such that when the effluent at the irrigation fluid outlet reaches the critical effluent temperature, the temperature inside the body cavity is at the critical thermal injury temperature at which cells or tissue of the body cavity will be subjected to thermal injuries.

In an alternative embodiment, the temperature sensor can be placed into the body cavity for monitoring the temperature directly inside the bladder. In one embodiment, the temperature sensor is inserted into the body cavity through a working port of the endoscope and disposed away from direct emission of the laser beam. In this embodiment, calibration of the temperature difference between the inside of the body cavity and at the irrigation fluid outlet is not needed.

In a further alternative embodiment, a remote temperature sensor, for example an inferred sensor, can also be used for the purpose of the present invention. A remote inferred temperature sensor is configured to monitor the temperature in the body cavity. One or more locations of the body cavity can be monitored, which reflects an overall temperature within the body cavity, a temperature at a particular vulnerable position, or both. Preferably, the inferred sensor is so positioned that the temperature detection is not interfered by the laser beam emitted during the laser ablation procedure.

Laser ablation surgery system 10 may further include one or more irrigation flow sensors 80 operably connected to the irrigation fluid inlet 56, the irrigation fluid outlet 58, or both of the flow sheath for monitoring the flow of the irrigation fluid during the surgery. The irrigation flow sensors are operably connected to system control 60. The system control comprises one or more predetermined irrigation flow criteria, and the system control is configured to activate the laser control mechanism 62 when at least one of the irrigation flow sensors 80 senses a violation of the predetermined irrigation flow criteria.

In one embodiment, the predetermined irrigation flow criteria is a minimum flow rate at the irrigation fluid inlet or outlet when the laser beam is emitted. Once the flow sensor 80 senses that the irrigation fluid inlet is below the minimum flow rate, the laser control mechanism 62 stops emission from the laser source 20. Moreover, the laser control mechanism 62 may also send a signal to indicate stopping of laser emission due to insufficient irrigation flow rate. If the irrigation fluid is not turned on accidently, or is blocked for some reason during a laser ablation surgery, continuing laser emission will cause further rising of the temperature in the body cavity adjacent to the target tissue due to heat transfer, and will cause thermal injury to the body cavity which is not the subject of the laser ablation. Using laser ablation surgery system 10 of the present invention, a surgeon will be immediately alerted if no irrigation fluid or insufficient irrigation fluid is provided to the body cavity adjacent to the target tissue at any time while the laser beam is emitted, which effectively prevents thermal injury to the body cavity due to insufficient cooling.

Moreover, one of the predetermined irrigation flow criteria can be a warning flow rate at the irrigation fluid inlet or outlet while the laser beam is emitted. Once the irrigation flow sensor senses a flow rate of the irrigation fluid reaching the warning flow rate, but not the minimum flow rate yet, the laser control mechanism 62 sends a warning signal so that an earlier preventative action can be taken by the surgeon.

In a further embodiment, system control 60 may further comprise an irrigation control mechanism 64 configured to adjust the flow rate of the irrigation fluid. Various flow regulating mechanisms can be used for the purpose of the present invention. In one embodiment, the irrigation fluid to the body cavity is provided using a flexible irrigation fluid bag as commonly used in prostate surgeries, a suction pump may be connected to the irrigation fluid outlet for regulating flow rate of the irrigation fluid. When the irrigation flow sensor senses the flow rate of the irrigation fluid is at the warning or minimum flow rate, the suction pump is activated by the system control 60 to enhance the outflow of the irrigation fluid in the body cavity, which in turn enhances the inflow of the irrigation fluid from the irrigation fluid bag.

In another embodiment, the irrigation fluid to the body cavity is provided with a pump connected to an irrigation fluid reservoir, and the inflow and outflow of the irrigation fluid are regulated. A suction pump at the outlet can be used together with the pump at the inlet. When the irrigation flow sensor senses the flow rate of the irrigation fluid is at the warning or minimum flow rate, system control 60 controls irrigation control mechanism 64 to regulate the flow rate accordingly. Moreover, system control 60 further monitors the difference between the inflow and outflow of the irrigation fluid and regulates the inflow and outflow accordingly to prevent an undesirable high or low pressure inside the body cavity. A proper flow rate range and allowable difference between the inflow and outflow can be preset in the system control. In the event that the flow rate is beyond a safe range, or the difference in the flow rate (in turn the fluid volume) exceeds the preset limit, system control 60 can also trigger a warning signal to alert the operator so that timely actions can be taken.

Figure 2:
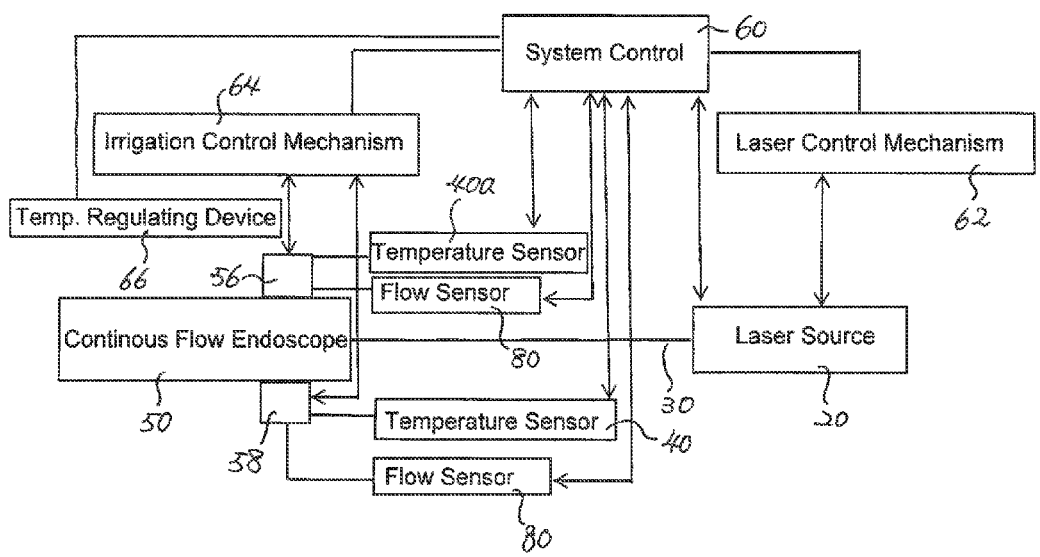
FIG. 2 is a schematic block diagram of the laser ablation surgery system in a further embodiment of the present invention.

In a further embodiment as shown in FIG. 2, a temperature sensor 40*a* is further provided at the irrigation fluid inlet and is configured to monitor the temperature of the irrigation fluid as it enters the endoscope. Temperature sensor 40*a* is operably connected to system control 60. System control 60 may further comprise a temperature regulating device 66 configured to adjust the temperature of the inflow irrigation fluid. Various known temperature regulating mechanisms can be used for the purpose of the present invention. In one embodiment, a semiconductor peltier is used to regulate the inflow irrigation fluid temperature.

Commonly, in a laser ablation surgery the irrigation fluid is warmed above room temperature before use to prevent hypothermia. However, warmed irrigation fluid has less cooling effect. In system 10, once temperature sensor 40 senses the effluent temperature is close to or at the warning effluent temperature, system control 60 can activate temperature regulating device 66 to cool the inflow irrigation fluid to increase the cooling efficiency of the irrigation fluid. At this time, because of the elevated temperature inside the body cavity and continuous heat transfer due to ongoing laser ablation, a cooled irrigation fluid at a desired temperature will not cause hypothermia. The temperature of inflow irrigation fluid is monitored by temperature sensor 40*a*, and system control 60 controls temperature regulating device 66 to adjust the temperature of inflow irrigation fluid according to the need of cooling as well as safety criteria such as a minimum temperature requirement. Once temperature sensor 40 senses the effluent temperature decrease to an acceptable level, system control 60 controls temperature regulating device 66 to stop or reduce cooling of the inflow irrigation fluid.

In yet a further embodiment, system 10 may further comprise a pressure sensor operably connected to system control 60. The pressure sensor is inserted into the body cavity through the working port of the endoscope to monitor the internal pressure in the body cavity periodically or in real time during the laser ablation procedure. System control 60 can further include one or more predetermined pressure thresholds, such as an upper threshold and a lower threshold. When the pressure sensor senses the internal pressure is above the upper threshold or below the lower threshold, system control 60 controls the irrigation control mechanism 64 to release or compensate for the internal pressure.

System 10 can be fully automated to monitor and control irrigation fluid temperature, flow rate, internal fluid pressure of the body cavity, and control laser emission according to the criteria and mechanisms described above.

Moreover, laser ablation surgery system 10 may further include an override mechanism, which allows the surgeon to override the laser control mechanism 62 under certain circumstances. For example, if the surgeon observes bleeding at the surgical site, while system control 60 stops the emission from the laser source 20 because the effluent reaches the effluent critical temperature, the surgeon can use the override mechanism to turn the laser source back on at a lower power output such as at a coagulation mode to timely cauterize the veins and stop bleeding.

The operation of laser ablation surgery system 10 is further described in reference to a photoselective vaporization of prostate (PVP) surgery for treating benign prostate hyperplasia. In a PVP surgery, optical fiber 30 is inserted into prostatic urethra through a working port in a continuous flow cystoscope 50, a particularly type of endoscope used by urologists for examining urethra and bladder. The laser source 20 through optical fiber 30 emits a laser beam at about 532 nm to the subject prostate, and the energy is transferred into heat that causes vaporization of excess prostate tissue. In the PVP surgery, an irrigation fluid is provided into the bladder through the flow sheath in the cystoscope for visualization and cooling the surrounding tissue of the surgical site during the laser ablation process. In this case, the bladder is a non-target tissue adjacent to the target tissue of the prostate.

In the laser ablation surgery, coagulation occurs as tissue temperature rises above 65° C. and vaporization occurs at 100° C. However, during laser vaporization procedure the tissue temperature may rise even higher. The actual temperature of the irrigant in the bladder during vaporization is a function of the temperature of the inflow fluid, the rate of inflow at the surgical site, and the rate of the outflow from the bladder. The area that is most vulnerable to thermal injury is close to the heat source, such as the anterior bladder wall where the steam from target tissue vaporization is in a constant contact with the surrounding irrigant, and the local temperature tends to exceed the critical thermal injury temperature. Irreversible changes and the severity of epithelial and deep tissue injury can be a function of the temperature to which the tissue is exposed to and duration of the exposure.

In one embodiment, a flexible bag of sterile saline solution is used as an irrigation fluid reservoir. A large bore tubing with a regulating clamp is connected to the irrigation fluid inlet and the inflow of the irrigation fluid is driven by gravity. The effluent exits the bladder through the flow sheath and flows out from the irrigation fluid outlet 58 disposed at the proximal end of the cystoscope. The effluent may flow naturally, as driven by the flow pressure due to the gravity driven inflow, or alternatively, may be withdrawn from the irrigation fluid outlet 58 by a suction pump of irrigation control mechanism 64.

The effluent temperature is substantially higher than normal body temperature due to heat transfer from the adjacent laser ablation of prostate. The temperature sensor 40 disposed at the irrigation fluid outlet monitors the effluent temperature during the entire process of the PVP surgery. In the event that a high power output of the laser source 20 is used for an uninterrupted extended period of time, such as more than 15-20 minutes, the steam generated by laser vaporization of the target tissue mixes with the irrigation fluid at the surgical site and enters the bladder, which causes the temperature inside the bladder to rise substantially. This is particularly the situation if the irrigation fluid flow rate is insufficient, then the temperature may rise to the extent that the bladder may incur a thermal injury. The substantially elevated temperature inside the bladder is reflected by the effluent temperature monitored at irrigation fluid outlet 58 by temperature sensor 40.

Using the system of the present invention, once the temperature sensor 40 senses that the effluent reaches a warning effluent temperature, the laser control mechanism 62 sends a warning signal to the surgeon, or automatically reduces the power output. If the laser ablation proceeds further and temperature sensor 40 senses that the effluent reaches the critical effluent temperature, laser control mechanism 62 immediately stops the emission from laser source 20 to prevent further rising of temperature in the bladder. Moreover, laser control mechanism 62 sends audio or visual warning signals to indicate the critical effluent temperature, as well as the stop of laser emission because of the critical effluent temperature. Therefore, the surgeon can take timely actions, such as increasing inflow of the irrigation fluid by adjusting the regulating clamp or elevating the irrigation solution bag, draining out the heated irrigation fluid inside the bladder, or trouble shooting the cause of insufficient irrigation fluid flow.

Moreover, during the surgery the flow sensor 80 at the irrigation fluid inlet 56, or irrigation fluid outlet 58, or both, monitors the flow rate of the irrigation fluid. In the situation that insufficient irrigation fluid flow is detected by the flow sensor 80, system control 60 takes actions as described above. For example, if the irrigation fluid runs out and needs a change to a new bag, or if the regulating clamp is not open inadvertently while the laser source 20 is on, system control 60 activates the laser control mechanism 62 immediately to stop laser source 20 from further emission. Therefore, system 10 of the present invention prohibits continuation of a PVP procedure in the absence of, or insufficient irrigation fluid to prevent potential severe thermal injury to the bladder due to heat transfer.

As can be appreciated, the safety measures provided by the system of the present invention effectively reduce potential risk of thermal injuries to the bladder in the PVP surgery, and reduce surgical complications associated with the exposure of the bladder to high temperature.

In a further embodiment, the method of the present invention can be alternatively implemented with a stand-alone temperature sensor disposed at the irrigation fluid outlet of the endoscope for a more manually controlled safety measure. The temperature sensor may include distinct markings for warning effluent temperature and critical effluent temperature. The temperature sensor may further provide audio or visual signals at these temperatures. In a laser ablation surgery the temperature sensor monitors the effluent temperature during the entire procedure. The surgeon or surgical staff can review the effluent temperature during the procedure and take actions when the temperature sensor indicates warning or critical effluent temperature, such as reducing laser power output, turning off laser source, increasing irrigation flow, draining out retained irrigation fluid in the body cavity, or other actions to prevent thermal injury to the body cavity.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A laser ablation surgery system with a safety control of non-target tissue temperature, the system comprising:
    (a) a laser source configured to produce a laser beam at a wavelength absorbable by a target issue through an optical fiber connected thereto;
    (b) a temperature sensor disposed at an irrigation fluid outlet of a flow sheath of a continuous flow endoscope, the continuous flow endoscope having an elongated probe including the flow sheath therein and with the irrigation fluid outlet of the flow sheath at a proximal end of the elongated probe, the temperature sensor being non-invasive and configured to monitor at the irrigation fluid outlet a temperature of an effluent of an irrigation fluid exiting a body cavity adjacent to the target issue during a laser ablation surgery thereby monitoring a temperature of the body cavity using the effluent as a medium, the body cavity being a non-target tissue not subject to ablation by the laser beam; and
    (c) a system control operably connected to the laser source and the temperature sensor, said system control comprising at least one predetermined effluent temperature threshold, and a laser control mechanism; the system control being configured to activate the laser control mechanism when the temperature sensor senses the temperature of the effluent exceeding the predetermined effluent temperature threshold.

2. The system of claim 1, wherein the predetermined effluent temperature threshold is a critical effluent temperature at which the body cavity sustains a thermal injury, and the laser control mechanism stops emission from the laser source when the temperature sensor senses the critical effluent temperature.

3. The system of claim 1, wherein the predetermined effluent temperature threshold is a warning effluent temperature below a critical effluent temperature at which the body cavity sustains a thermal injury, and the laser control mechanism sends a warning signal to the user, or reduces laser emission from the laser source when the temperature sensor senses the warning effluent temperature.

4. The system of claim 1, wherein the system further comprises one or more irrigation flow sensors disposed at an irrigation fluid inlet at the proximal end of the elongated probe, the irrigation fluid outlet, or both of the flow sheath, and operably connected to the system control, and the system control comprises at least one predetermined irrigation flow criteria, and wherein the system control activates the laser control mechanism when the one or more irrigation flow sensors sense a violation of the predetermined irrigation flow criteria.

5. The system of claim 4, wherein the predetermined irrigation flow criteria is a minimum flow rate at the irrigation fluid inlet or outlet while the laser beam is emitted, and the laser control mechanism stops emission from the laser source when the irrigation flow sensor senses a flow rate of the irrigation fluid below the minimum flow rate.

6. The system of claim 4, wherein the predetermined irrigation flow criteria is a warning flow rate at the irrigation fluid inlet or outlet while the laser beam is emitted, and the laser control mechanism sends a warning signal when the irrigation flow sensor senses a flow rate of the irrigation fluid at the warning flow rate.

7. The system of claim 4, wherein the system control further comprises an irrigation control mechanism configured to adjust a flow rate of the irrigation fluid when the irrigation flow sensor senses a violation of the predetermined irrigation flow criteria.

8. The system of claim 1, wherein the continuous flow endoscope is a continuous flow cystoscope, and the target tissue is prostate and the body cavity is the bladder.

9. The method of claim 1, wherein the temperature sensor is remote from the target tissue and not exposed to the laser beam emitted through the optical fiber during the laser ablation surgery.

10. A method of laser ablation surgery comprising:
    (a) performing a laser ablation surgery on a target tissue using a laser ablation surgery system, said system comprising:
        (i) a laser source configured to produce a laser beam at a wavelength absorbable by a target issue through an optical fiber connected thereto;
        (ii) a temperature sensor disposed at an irrigation fluid outlet of a flow sheath of a continuous flow endoscope, the continuous flow endoscope having an elongated probe including the flow sheath therein and with the irrigation fluid outlet of the flow sheath at a proximal end of the elongated probe, the temperature sensor being non-invasive and configured to monitor at the irrigation fluid outlet a temperature of an effluent of an irrigation fluid exiting a body cavity adjacent to the target issue during a laser ablation surgery thereby monitoring a temperature of the body cavity using the effluent as a medium, the body cavity being a non-target tissue not subject to ablation by the laser beam; and (iii) a system control operably connected to the laser source and the temperature sensor, said system control comprising at least one predetermined effluent temperature threshold, and a laser control mechanism; and (b) monitoring at the irrigation fluid outlet the temperature of the effluent exiting the body cavity during the laser ablation surgery by the temperature sensor, wherein the system control activates the laser control mechanism when the temperature sensor senses the temperature of the effluent exceeding the at least one predetermined effluent temperature threshold, thereby preventing a thermal injury to the body cavity due to heat transfer.

11. The method of claim 10, wherein the system further comprises one or more irrigation flow sensors disposed at an irrigation fluid inlet at the proximal end of the elongated probe, the irrigation fluid outlet, or both of the flow sheath, and operably connected to the system control, and the system control comprises at least one predetermined irrigation flow criteria; and wherein the method further comprises activating the laser control mechanism when the one or more irrigation flow sensors senses a violation of the at least one predetermined irrigation flow criteria.

12. The method of claim 10, wherein the laser ablation surgery is a photoselective vaporization of prostate surgery, the target tissue is prostate, and the body cavity is the bladder.

13. The system of claim 10, wherein the temperature sensor is remote from the target tissue and not exposed to the laser beam emitted through the optical fiber during the laser ablation surgery.

14. A method of laser ablation surgery comprising:
(a) performing a laser ablation surgery on a target tissue with a continuous flow endoscope using an optical fiber connected to a laser source configured to produce a laser beam at a wavelength absorbable by the target issue;

(b) providing a temperature sensor at an irrigation fluid outlet of the continuous flow endoscope, the continuous flow endoscope having an elongated probe including the flow sheath therein and with the irrigation fluid outlet of the flow sheath at a proximal end of the elongated probe, the temperature sensor being non-invasive and configured to monitor at the irrigation fluid outlet a temperature of an effluent of an irrigation fluid exiting a body cavity adjacent to the target tissue thereby monitoring a temperature of the body cavity using the effluent as a medium, the body cavity being a non-target tissue not subject to ablation by the laser beam; and (c) monitoring at the irrigation fluid outlet the temperature of the effluent exiting the body cavity by the temperature sensor during the laser ablation surgery on the target tissue, and adjusting emission of the laser source when the temperature sensor senses the temperature of the effluent exceeding a predetermined effluent temperature threshold, thereby preventing a thermal injury to the body cavity due to heat transfer.

15. The method of claim 14 further comprising providing a flow sensor at an irrigation fluid inlet at the proximal end of the elongated probe of the continuous flow endoscope, monitoring a flow rate of the irrigation fluid entering the body cavity during the laser ablation surgery, and adjusting emission of the laser source when the flow sensor senses the flow rate of the irrigation fluid below a predetermined minimum flow rate.

16. The method of claim 14, wherein the laser ablation surgery is a photoselective vaporization of prostate surgery, the target tissue is prostate, and the body cavity is the bladder.

17. The method of claim 14, wherein the temperature sensor is remote from the target tissue and not exposed to the laser beam emitted through the optical fiber during the laser ablation surgery.

* * * * *

UNITED STATES PATENT AND TRADEMARK OFFICE
CERTIFICATE OF CORRECTION

PATENT NO. : 9,956,040 B1
APPLICATION NO. : 14/866996
DATED : May 1, 2018
INVENTOR(S) : Emilio F. Lastarria Page 1 of 1

It is certified that error appears in the above-identified patent and that said Letters Patent is hereby corrected as shown below:

On the Title Page

In the Abstract
Line 5, change "issue" to --tissue--
Line 11, change "issue" to --tissue--

In the Specification

Column 2, Line 39, change "issue" to --tissue--
Column 2, Line 44, change "issue" to --tissue--
Column 3, Line 2, change "issue" to --tissue--
Column 3, Line 41, change "issue" to --tissue--
Column 4, Line 26, change "issue" to --tissue--
Column 4, Line 31, change "issue" to --tissue--

In the Claims

Claim 1, Column 9, Line 50, change "issue" to --tissue--
Claim 1, Column 9, Line 61, change "issue" to --tissue--
Claim 10, Column 10, Line 59, change "issue" to --tissue--
Claim 10, Column 11, Line 3, change "issue" to --tissue--
Claim 14, Column 12, Line 3, change "issue" to --tissue--

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*